US006262268B1

(12) United States Patent
Palucki et al.

(10) Patent No.: US 6,262,268 B1
(45) Date of Patent: Jul. 17, 2001

(54) PROCESS AND INTERMEDIATES TO A TETRAHYDRO-[1,8]-NAPHTHYRIDINE

(75) Inventors: Michael Palucki, Belle Mead; David L. Hughes, Hoboken; Chunhua Yang, Edison; Nobuyoshi Yasuda, Mountainside, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/709,083

(22) Filed: Nov. 9, 2000

Related U.S. Application Data

(60) Provisional application No. 60/164,605, filed on Nov. 10, 1999.

(51) Int. Cl.$^7$ .................. C07D 213/38; C07D 401/14; C07D 471/04
(52) U.S. Cl. ............... 546/122; 546/277.1; 546/329
(58) Field of Search ................ 546/122, 277.1, 546/329

(56) References Cited

U.S. PATENT DOCUMENTS

| | | |
|---|---|---|
| 5,952,341 | 9/1999 | Duggan et al. . |
| 6,017,926 | 1/2000 | Askew et al. . |
| 6,048,861 | 4/2000 | Askew et al. . |

FOREIGN PATENT DOCUMENTS

| | | |
|---|---|---|
| WO 98/18460 | 5/1998 | (WO) . |
| WO 99/31061 | 6/1999 | (WO) . |
| WO 99/31099 | 6/1999 | (WO) . |

OTHER PUBLICATIONS

Hawes et al., "1,8–Naphthyridines", J. Chem. Soc., pp. 315–321, (1966).

Hawes et al., "Intramolecular Nucleophilic Cyclization of 3–Substituted Pyridylalkylamines onto the 2–Position of the Pyridine Ring", J. Heterocyclic Chem., vol. 10, pp. 39–42 (1973).

Breuker et al., "The Chichibabin amination of 4–phenyl–and 4–tert–butyl–pyrimidine", Recl. Trav. Chim. PAYS–BAS, vol. 102, pp. 367–372 (1983).

Vajda et al., "Direct Substitution in Pyridine Ring Systems By Basic Reagents", Recl. Trav. Chim. PAYS–BAS, vol. 80, pp. 47–56 (1961).

*Primary Examiner*—Bernard Dentz
(74) *Attorney, Agent, or Firm*—Philippe L. Durette; Melvin Winokur

(57) ABSTRACT

A novel process is provided for the preparation of 3-(5,6,7,8-tetrahydro-[1,8]-naphthyridin-2-yl)-propylamine which is useful in the synthesis of αv integrin receptor antagonists. Also provided are useful intermediates obtained from the process.

30 Claims, No Drawings

PROCESS AND INTERMEDIATES TO A TETRAHYDRO-[1,8]-NAPHTHYRIDINE

CROSS-REFERENCE TO RELATED APPLICATIONS

The present application claims priority of U.S. provisional application Ser. No. 60/164,605, filed Nov. 10, 1999, the contents of which is hereby incorporated by reference.

FIELD OF THE INVENTION

The present invention discloses a novel process and novel intermediates toward the preparation of 3-(5,6,7,8-tetrahydro-[1,8]-naphthyridin-2-yl)-propylamine which is useful in the synthesis of αv integrin receptor antagonists.

BACKGROUND OF THE INVENTION

The present invention provides an improved process for the preparation of 3-(5,6,7,8-tetrahydro-[1,8]-naphthyridin-2-yl)-propylamine (I).

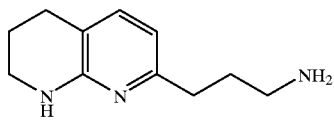

The present invention also provides intermediates useful in the disclosed process.

The synthesis of compound (I) has previously been disclosed in U.S. Pat. No. 6,048,861 (Apr. 11, 2000); U.S. Pat. No. 5,952,341 (Sep. 14, 1999); WO 98/18460; and WO 99/31061. In these references, the naphthyridine ring is constructed by way of a Friedländer reaction between 2-amino-3-formyl-pyridine and 2-oxo-5-(benzyloxycarbonylamino)-pentane or 2-oxo-5-(t-butyloxycarbonylamino)-pentane. The described procedures involve a total of seven chemical transformations, several chromatographic purifications, and an overall yield of about 38%.

In the present invention, compound (I) is produced highly efficiently in a total of three chemical steps from a protected allylamine with an improved overall yield of about 76%. The method features a one-pot double Suzuki cross-coupling of a 2,5-dihalopyridine with a protected allylamine, deprotection, and a highly regioselective intramolecular Chichibabin-type cyclization to afford the final product (I).

SUMMARY OF THE INVENTION

This invention is concerned with a process for preparing 3-(5,6,7,8-tetrahydro-[1,8]-naphthyridin-2-yl)-propylamine of structural formula (I) and certain useful intermediates obtained during that process. The process utilizes a double Suzuki reaction of a 2,5-dihalopyridine with a protected allylamine, deprotection, and an intramolecular Chichibabin reaction.

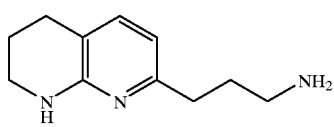

The novel process and novel intermediates are illustrated in the following embodiment denoted in Scheme 1 below.

Scheme 1

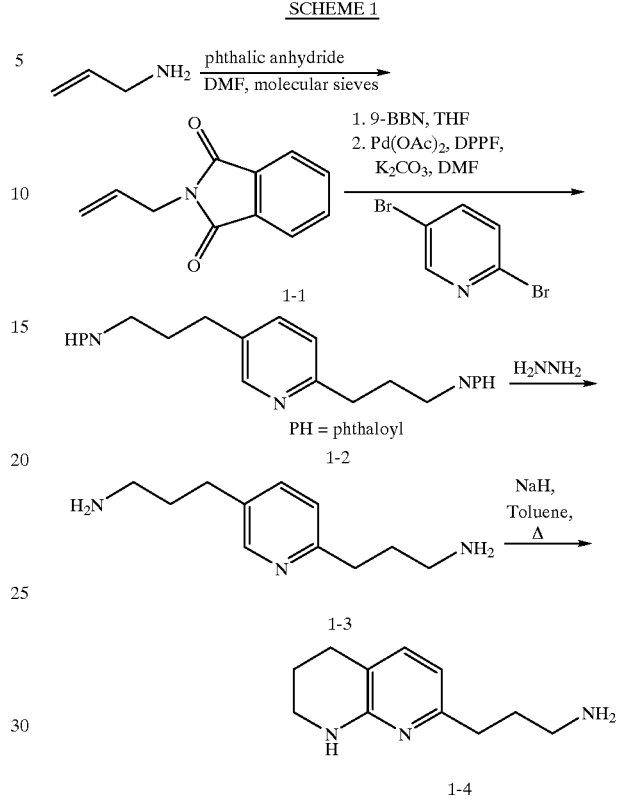

As disclosed in U.S. Pat. No. 6,048,861 (Apr. 11, 2000); U.S. Pat. No. 5,952,341 (Sep. 14, 1999); WO 98/18460; and WO 99/31061, compound (I) is a key intermediate in the synthesis of αv integrin receptor antagonists which are useful for inhibiting bone resorption and therefore for treating and/or preventing osteoporosis.

DETAILED DESCRIPTION OF THE INVENTION

The process of the present invention involves the preparation of the compound of structural formula (I):

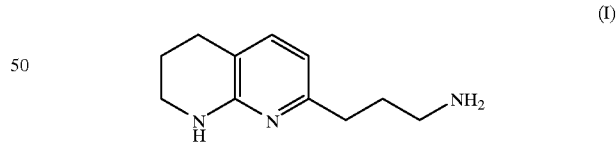

comprising the steps of:
(a) producing a compound of structural formula (III):

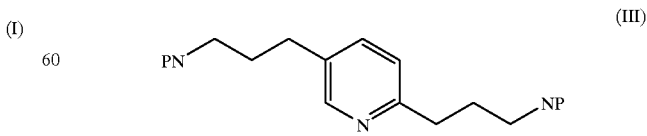

wherein P is an amine protecting group, by treating a 2,5-dihalopyridine with a protected allylamine of structural formula (IV):

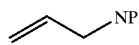

in an organic solvent B, in the presence of a hydroboration reagent, a palladium catalyst, a phosphine ligand, and a proton acceptor;

(b) producing the compound of structural formula (II):

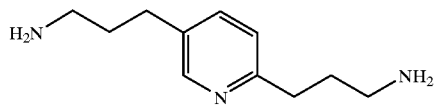

by cleaving the amine protecting groups P in a compound of structural formula (III):

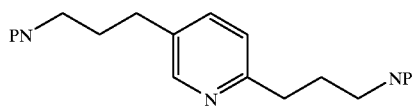

wherein P is amine protecting group;

(c) treating the compound of structural formula (II):

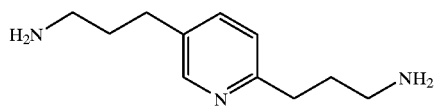

with base in an organic solvent A; and (d) isolating the resulting product (I).

The key steps of the above process of the present invention include a double Suzuki reaction of a 2,5-dihalopyridine with a protected allylamine, deprotection, and an intramolecular Chichibabin-type cyclization reaction.

One substrate for the double Suzuki reaction is an appropriately protected allylamine. In one embodiment of the process of the present invention, the allylamine is protected as its phthalimide derivative. This is accomplished by treatment of allylamine with phthalic anhydride in a suitable solvent, such as DMF. However, other amine protecting groups may also be used and include t-butyloxycarbonyl (Boc), benzyloxycarbonyl (Cbz), 9-fluorenylmethyloxycarbonyl (FMOC), allyloxycarbonyl (Alloc), acetyl, benzoyl, and pivaloyl. Reference is made to T. W. Greene and P. G. M. Wuts, *Protective Groups in Organic Synthesis*, 2$^{nd}$ Edition (1991) for a description of other amine protecting groups which may be employed in the present process.

The second Suzuki coupling partner is a 2,5-dihalopyridine. In one embodiment, the 2,5-dihalopyridine is 2,5-dibromopyridine. However, 2,5-dichloropyridine, 2,5-diiodopyridine, or a mixed 2,5-dihalopyridine, such as 2-chloro-5-bromo-pyridine, may also be employed in the reaction. A further optional Suzuki coupling partner for the protected allylamine is 2,5-di-(trifluoromethanesulfonyloxy)pyridine.

The double Suzuki reaction of a 2,5-dihalopyridine is effected with the hydroborated product resulting from the reaction of a hydroboration reagent with the protected allylamine in a suitable solvent in the presence of a palladium catalyst, a proton acceptor, and a phosphine ligand. In one embodiment of this step of the process, the hydroboration reagent is 9-BBN. However, other boron reagents may also be used and include disiamylborane, dicyclohexylborane, and borane. In a second embodiment of this step, the phosphine ligand is DPPF. However, other phosphine ligands may also be employed and include triphenylphosphine, tri(o-tolyl)phosphine, DPPE, and DPPP.

Palladium catalysts which may be used in the Suzuki reaction include a palladium alkanoate, a palladium acetonate, a palladium halide, a palladium halide complex, a palladium-dibenzylidene acetone complex, and a triarylphosphine palladium complex. More specifically, the palladium catalyst is selected from the group consisting of Pd(II) acetate, Pd(II) acetylacetonate, Pd(O)bis-dibenzylidene acetone ("dba"), Pd(II) bromide, Pd(II) chloride, Pd(II) iodide, Pd(II) sulfate, Pd(II) trifluoroacetate, Pd(II) Cl$_2$(CH$_3$CN)$_2$, Pd$_2$(dba)$_3$, Pd(dppf)Cl$_2$, PdCl$_2$(PPh$_3$)$_2$, Pd(PPh$_3$)$_4$, and Pd(II)Cl$_2$(PhCN)$_2$. In one embodiment the palladium catalyst is Pd(II) acetate.

The Suzuki reaction is carried out in a suitable organic solvent B, such as THF, benzene, toluene, dioxane, DME, DMSO, DMF, DMAC, and NMP, or a mixture of these solvents, such as THF/DMF. In one embodiment, the organic solvent B is DMF. The reaction is carried out in the presence of a proton acceptor, which includes an organic base, such as alkylamine, in particular triethylamine or diisopropylethylamine, and an inorganic base, such as potassium carbonate, sodium carbonate, sodium hydrogencarbonate, potassium phosphate (K$_3$PO$_4$), an alkali metal alkoxide such as sodium methoxide, and aqueous sodium or potassium hydroxide. In one embodiment, the base is powdered potassium carbonate. The reaction is performed at a temperature range of about 25° C. to 80° C. In another embodiment, the protected allylamine is used in an amount of about 2 to 3 molar equivalents of the 2,5-dihalopyridine. In a further embodiment, the "active" Pd-catalyst is generated separately via heating a solution of Pd(II) acetate and DPPF in DMF for 30 to 60 minutes instead of adding Pd(II) acetate, DPPF, and DMF separately to the reaction mixture.

The double Suzuki cross-coupling reaction product is a compound of structural formula (III):

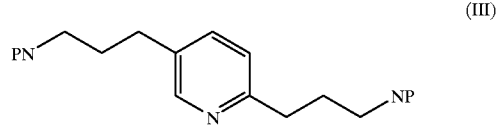

wherein P is an amine protecting group. The next step of the process of the present invention is the removal of the protecting groups P in substrate (III) to generate compound (II). When the amine protecting group is phthaloyl, it may be cleaved by treatment with aqueous hydrazine in an alcoholic solvent, such as refluxing ethanol, or with an alkylamine, such as methylamine in methanol or ethanol, preferably at an elevated temperature. In one embodiment, the phthaloyl group is cleaved with hydrazine in refluxing ethanol. When the amine protecting group is t-butyloxycarbonyl, it may be cleaved by treatment with trifluoroacetic acid, sulfuric acid, HCl in ethyl acetate, HCl in diethyl ether, or HCl in dioxane. Other protecting groups are removed by standard literature conditions, such as those found in T. W. Greene and P. G. M. Wuts, *Protective Groups in Organic Synthesis*, 2$^{nd}$ Edition (1991).

The final step in the process of the present invention is the cyclization of compound (II) to elaborate the final product (I). This intramolecular transformation is efficiently carried out by an optimized Chichibabin-type reaction (for a discussion of Chichibabin aminations, see H. Vorbrüggen, *Adv. Heterocyclic Chem.*, 49, 1990, 117–192). Intramolecular nucleophilic cyclizations of 3-substituted pyridylalkylamines have previously been described. Thus, treatment of 3-(3-pyridyl)propylamine with two equivalents of sodium in boiling toluene afforded 1,2,3,4-tetrahydro-[1,8]-naphthyridine in 30% yield (E. M. Hawes and H. L. Davis, *J. Heterocyclic Chem.*, 1973, 39–42). 1,2,3,4-Tetrahydro-3-phenyl-[1,8]-naphthyridine has been similarly prepared in 54% yield (E. M. Hawes and D. G. Wibberley, *J. Chem. Soc.* (C), 1966, 315–321). The substrate for the Chichibabin-reaction of the present invention has two nucleophilic amino groups presenting complicating issues of regioselectivity and intramolecular vs. intermolecular reactivity.

In the method of the present invention, compound (II) is converted into compound (I) by treating (II) in an organic solvent A with a suitable base at elevated temperatures. The organic solvent A is selected from the group consisting of toluene, tetrahydrofuran, chlorobenzene, diisopropylethylamine, DMPU, and mixtures thereof. In one embodiment, the organic solvent A is toluene. A suitable base is selected from the group consisting of an alkali metal such as sodium metal, an alkali metal hydride such as sodium or lithium hydride, an alkyl lithium such as n-butyl lithium, an alkali metal hexamethyldisilazide, such as potassium or sodium hexamethyldisilazide (KHMDS), and an alkali metal amide, such as lithium amide, sodium amide, or potassium amide. In one embodiment of the present invention, the base is sodium amide. In a class of this embodiment, the sodium amide is used in an amount of about 2 to 5 equivalents relative to compound (II). In another embodiment, the cyclization reaction is carried out at a temperature range of about 60° C. to 115° C. In a class of this embodiment, the reaction is carried out at a temperature of about 90° C.

Further embodiments of this invention comprise the following novel compounds which are intermediates in the preparation of compound (I):

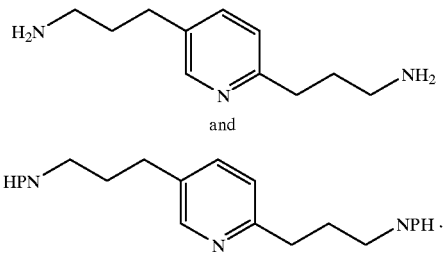

PH = phthaloyl

Representative experimental procedures utilizing the novel process are detailed below. For purposes of illustration, the following Example is directed to the preparation of compound (I), but doing so is not intended to limit the process of the present invention to the specific conditions for making the compound.

Abbreviations: AcOH is acetic acid; 9-BBN is 9-borabicyclo[3.3.1]nonane; BuLi is n-butyl lithium; $CH_2Cl_2$ is dichloromethane; DMAC is N,N-dimethylacetamide; DME is 1,2-dimethoxyethane; DMF is N,N-dimethylformamide; DMPU is 1,3-dimethyl-3,4,5,6-tetrahydro-2(1H)-pyrimidinone; DMSO is dimethyl sulfoxide; DPPE is diphenylphosphinoethane; DPPF is diphenylphosphinoferrocene; DPPP is diphenylphosphinopropane; EtOAc is ethyl acetate; $Et_3N$ is triethylamine; $K_2CO_3$ is potassium carbonate; $MgSO_4$ is magnesium sulfate; MTBE is methyl t-butyl ether; NMP is N-methylpyrrolidinone; NMR is nuclear magnetic resonance; $Na_2CO_3$ is sodium carbonate; $NaHCO_3$ is sodium hydrogencarbonate; $P(otol)_3$ is tri-o-tolyl-phosphine; and THF is tetrahydrofuran.

By halo is meant chloro, bromo, or iodo.

EXAMPLE 3-(5,6,7,8-Tetrahydro-[1,8]-naphthyridin-2-yl)-propylamine (1-4)

Step A: Preparation of N-allylphthalimide (1-1)

A 500 mL round-bottom flask was charged with phthalic anhydride (22.2 g, 150 mmol) and anhydrous DMF (150 mL) and stirred at room temperature for 5 min to dissolve the phthalic anhydride. To the solution was slowly added allylamine (11.26 mL, 150 mmol) followed by 20 g of 3A molecular sieves. The resulting mixture was stirred at room temperature 10 minutes and then heated under nitrogen at 80° C. for 16 hrs. The reaction mixture was cooled to room temperature and filtered. To the mother liquor was added 300 mL of EtOAc and 300 mL of brine solution. The organic layer was separated, washed twice with 300 mL of water, and dried over $MgSO_4$. The drying agent was removed by filtration and the mother liquor concentrated. The resulting solid was recrystalized from $CH_2Cl_2$/hexane to yield 27.75 g (98% yield) of N-allylphthalimide (1-1).

Step B: Preparation of 2,5-di-(3-phthaloylaminopropyl)-pyridine (1-2)

An oven dried, $N_2$-purged 500 mL round-bottom flask equipped with an addition funnel, $N_2$ inlet and septum was charged with N-allylphthalimide (1-1) (1.79 g, 9.57 mmol) and 4.3 mL of anhydrous THF. The mixture was stirred for 5 minutes to dissolve the N-allylphthalimide and then cooled to 0° C. To this mixture was slowly added a 0.5M THF solution of 9-BBN (23 mL, 11.49 mmol). The resulting yellow solution was stirred overnight under $N_2$ at room temperature (14 hrs). After stirring overnight, the flask was charged with 2,5-dibromopyridine (1.0 g, 4.31 mmol) and finely grounded $K_2CO_3$ (1.98 g, 14.35 mmol). Separately, a 25 mL flask was charged with $Pd(OAc)_2$ (97 mg, 0.43 mmol), DPPF (286 mg, 0.54 mmol) and anhydrous DMF (10 mL). The mixture was stirred at 70° C. for 1 h and then transferred by cannula to the reaction mixture. The resulting orange/red solution was placed in an 70° C. oil bath. The reaction was stirred at the indicated temperature until completion (8–15 hrs). Upon completion, 150 mL of $CH_2Cl_2$ and 150 mL of saturated $NaHCO_3$ were added. The organic layer was separated, washed with 150 mL of water and dried over $MgSO_4$. The drying agent was removed by filtration and the mother liquor concentrated. Silica gel chromatography (75% EtOAc/hexane, Rf=.26) on the resulting residue yielded 1.65 g of the title compound 1-2 (84.4% yield).

Step C: Preparation of 2,5-di-(3-aminopropyl)pyridine (1-3)

A 250 mL round-bottom flask was charged with compound 1-2 (1.46 g, 3.22 mmol), EtOH (35 mL), and a 35% solution of hydrazine (1.47 g, 16.1 mmol). The resulting mixture was heated to reflux for 5 hrs. The mixture was cooled to room temperature and then acidified using conc. HCl to pH about 1. The mixture was then heated to reflux for 45 minutes (a significant amount of solids formed at this point). After cooling to room temperature, the solution was filtered and the mother liquor was concentrated to approximately 5 mL. To this was added 2M HCl (20 mL) and 20 mL of MTBE. The aqueous layer was separated and made basic using 5N NaOH. The resulting solution was extracted 5×200 mL of $CH_2Cl_2$. Concentration of the organic phase resulted in 0.6 g (97% yield) of the desired 2,5-(3-aminopropyl) pyridine (1-3).

Step D: Preparation of 3-(5,6,7,8-tetrahydro-[1,8]-naphthyridin-2-yl)propylamine (1-4)

A 100 mL round-bottom flask equipped with a $N_2$ inlet was charged with 1-3 (2.54 g, 13.1 mmol), toluene (65 mL), and freshly grounded $NaNH_2$ (2.69 g, 65.5 mmol). The flask was evacuated and back filled with $N_2$ and placed in a 90° C. oil bath. After 15 h, water (1.18 mL, 65.5 mmol) was added slowly without removing the flask from the oil bath. Caution: an exothermic reaction occurs upon addition of water. After the addition of water, the resulting mixture was filtered while hot, followed by 65 mL of hot toluene (90° C.). The mother liquor was concentrated to yield 2.37 g (94%) of 1-4.

$^1$H NMR ($CDCl_3$, 400 MHz) δ1.56 (bs, 1H) 1.78 (t, J=7.5 Hz, 2H), 1.88 (t, J=5.7 Hz, 2H), 2.55 (t, J=7.4 Hz, 2H), 2.65–2.72 (m, 4H), 3.37 (t, J=5.0 Hz, 2H), 4.89 (bs, 1H), 6.33 (d, J=7.3 Hz, 2H), 7.03 (d, J=7.3 Hz, 2H).

$^{13}$C NMR ($CDCl_3$, 100 MHz) δ21.4, 26.2, 33.8, 35.0, 41.4, 41.7, 110.9, 112.9, 136.4, 155.7, 157.8.

What is claimed is:

1. A process for preparing the compound of structural formula (I):

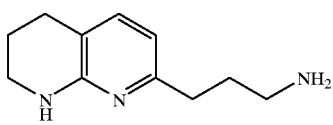

(I)

comprising the step of treating the compound of structural formula (II):

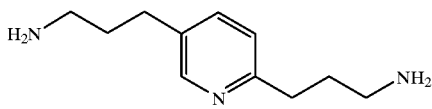

(II)

with base in an organic solvent A, and isolating the resulting product (I).

2. The process of claim 1 additionally comprising the step of producing the compound of structural formula (II):

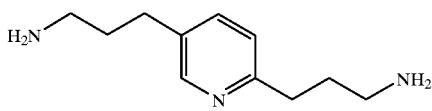

(II)

by cleaving the amine protecting groups P in a compound of structural formula (III):

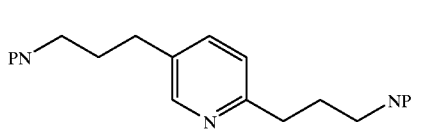

(III)

wherein P is amine protecting group, and isolating the resulting product (II).

3. The process of claim 2 additionally comprising the step of producing a compound of structural formula (III):

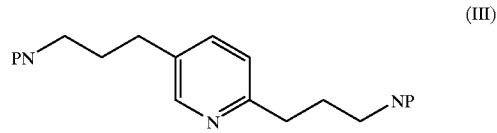

(III)

wherein P is an amine protecting group, by treating a 2,5-dihalopyridine with a protected allylamine of structural formula (IV):

(IV)

in an organic solvent B, in the presence of a hydroboration reagent, a palladium catalyst, a phosphine ligand, and a proton acceptor, and isolating the resulting product.

4. The process of claim 1 wherein the base is selected from the group consisting of an alkali metal, an alkali metal hydride, an alkyl lithium, an alkali metal hexamethyldisilazide, and an alkali metal amide.

5. The process of claim 1 wherein the organic solvent A is selected from the group consisting of toluene, tetrahydrofuran, chlorobenzene, diisopropylethylamine, DMPU, and mixtures thereof.

6. The process of claim 4 wherein the alkali metal amide is lithium amide or sodium amide.

7. The process of claim 5 wherein the organic solvent A is toluene.

8. The process of claim 1 wherein the reaction is carried out at a temperature of about 60° C. to 115° C.

9. The process of claim 3 wherein the palladium catalyst is selected from the group consisting of a palladium alkanoate, a palladium acetonate, a palladium halide, a palladium halide complex, a palladium-dibenzylidene acetone complex, and a triarylphosphine palladium complex.

10. The process of claim 9 wherein the palladium catalyst is selected from the group consisting of Pd(II) acetate, Pd(II) acetylacetonate, Pd(0)bis-dibenzylidene acetone ("dba"), Pd(II) bromide, Pd(II) chloride, Pd(II) iodide, Pd(II) sulfate, Pd(II) trifluoroacetate, Pd(II) $C_2(CH_3CN)_2$, $Pd_2(dba)_3$, $Pd(dppf)Cl_2$, $PdCl_2(PPh_3)_2$, $Pd(PPh_3)_4$, and $Pd(II)Cl_2(PhCN)_2$.

11. The process of claim 10 wherein the palladium catalyst is Pd(II) acetate.

12. The process of claim 3 wherein the phosphine ligand is selected from the group consisting of triphenylphosphine, tri(o-tolyl)phosphine, DPPE, DPPF, and DPPP.

13. The process of claim 3 wherein the proton acceptor is an alkylamine or an inorganic base.

14. The process of claim 13 wherein the inorganic base is $K_2CO_3$, $Na_2CO_3$, $K_3PO_4$, or aqueous sodium or potassium hydroxide.

15. The process of claim 3 wherein the organic solvent B is selected from the group consisting of THF, benzene, toluene, dioxane, DME, DMSO, DMF, DMAC, and NMP.

16. The process of claim 15 wherein the organic solvent B is DMF.

17. The process of claim 3 wherein the 2,5-dihalopyridine is 2,5-dibromopyridine.

18. The process of claim 3 wherein the reaction is carried out at a temperature of about 25° C. to 80° C.

19. The process of claim 3 wherein the hydroboration reagent is selected from the group consisting of 9-BBN, disiamylborane, dicyclohexylborane, and borane.

20. The process of claim 19 wherein the hydroboration reagent is 9-BBN.

21. The process of claim 2 wherein the amine protecting group P is selected from the group consisting of phthaloyl, benzyloxycarbonyl, t-butyloxycarbonyl, allyloxycarbonyl, 9-fluorenylmethyloxycarbonyl, acetyl, benzoyl, and pivaloyl.

22. The process of claim 21 wherein the amine protecting group P is phthaloyl.

23. The process of claim 22 wherein the phthaloyl protecting group is cleaved with hydrazine.

24. The process of claim 21 wherein the amine protecting group P is t-butyloxycarbonyl.

25. The process of claim 24 wherein the t-butyloxycarbonyl protecting group is cleaved with trifluoroacetic acid.

26. The process of claim 3 wherein the said protected allylamine is used in an amount of about 2 to 3 molar equivalents of said 2,5-dihalopyridine.

27. A process for preparing the compound of structural formula (I):

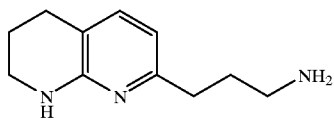

(I)

comprising the steps of:

(a) producing a compound of structural formula (III):

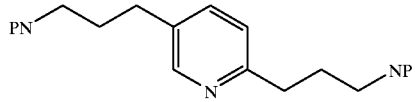

(III)

wherein P is an amine protecting group, by treating a 2,5-dihalopyridine with a protected allylamine of structural formula (IV):

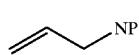

(IV)

in an organic solvent B, in the presence of a hydroboration reagent, a palladium catalyst, a phosphine ligand, and a proton acceptor;

(b) producing the compound of structural formula (II):

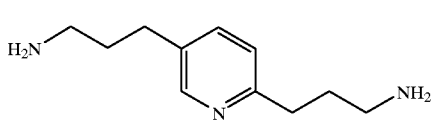

(II)

by cleaving the amine protecting groups P in a compound of structural formula (III):

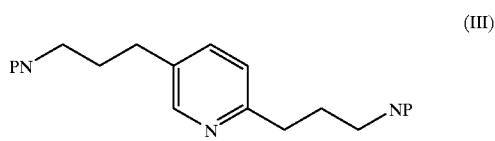

(III)

wherein P is amine protecting group;

(c) treating the compound of structural formula (II):

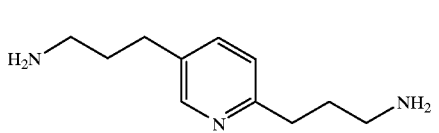

(II)

with base in an organic solvent A; and (d) isolating the resulting product (I).

28. A compound selected from

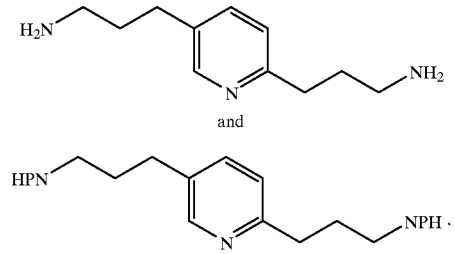

PH = phthaloyl

29. The process of claim 6 wherein the alkali metal amide is used in an amount of about 2 to 5 molar equivalents of compound of structural formula (II).

30. The process of claim 8 wherein the reaction is carried out at a temperature of about 90° C.

* * * * *